United States Patent
Kaltenbronn et al.

[11] Patent Number: 6,143,766
[45] Date of Patent: Nov. 7, 2000

[54] BENZOPYRANONE AND QUINOLONE INHIBITORS OF RAS FARNESYL TRANSFERASE

[75] Inventors: James Stanley Kaltenbronn; Daniele Marie Leonard; Joseph Thomas Repine, all of Ann Arbor, Mich.

[73] Assignee: Warner-Lambert Company, Morris Plains, N.J.

[21] Appl. No.: 09/488,437

[22] Filed: Jan. 20, 2000

Related U.S. Application Data

[60] Provisional application No. 60/129,586, Apr. 16, 1999.

[51] Int. Cl.[7] .................. A61K 31/47; A61K 31/415; C07D 215/16; C07D 233/02
[52] U.S. Cl. .................. 514/312; 514/397; 546/157; 548/311.4
[58] Field of Search .................. 514/312, 397; 546/157; 548/311.4

[56] References Cited

U.S. PATENT DOCUMENTS

| | | | |
|---|---|---|---|
| 4,690,932 | 9/1987 | Kojima | 514/337 |
| 5,073,563 | 12/1991 | Frickel | 514/365 |
| 5,227,392 | 7/1993 | Frickel | 514/363 |

FOREIGN PATENT DOCUMENTS

| | | | |
|---|---|---|---|
| 97/16443 | 5/1997 | WIPO | C07D 401/06 |
| 97/21701 | 6/1997 | WIPO | C07D 401/06 |
| 98/40383 | 9/1998 | WIPO | C07D 471/06 |

OTHER PUBLICATIONS

Abyshev, A. Z., et al., "Synthesis and Biological Activity of Derivatives of Benzopyran–2–One", *Pharm. Chem. J.*, vol. 27, No. 11, 1993, pp. 766–770.

Abyshev, A. Z., et al., "Synthesis and Biological Activity of Benzopyran–2–one Derivatives", *Russia Khim–Farm. Zh.*, vol. 27, No. 11, 1993, pp. 34–38.

*Primary Examiner*—D. Margaret Seaman
*Attorney, Agent, or Firm*—Charles W. Ashbrook

[57] ABSTRACT

The present invention provides ras farnesyl transferase inhibiting compounds of Formula I

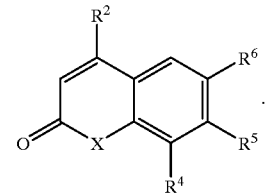

The present invention also provides a method of treating cancer and treating or preventing restenosis or atherosclerosis. Also provided by the present invention is a pharmaceutically acceptable composition containing a compound of Formula I.

14 Claims, No Drawings

BENZOPYRANONE AND QUINOLONE INHIBITORS OF RAS FARNESYL TRANSFERASE

This application claims priority to Provisional Application 60/129,586, filed Apr. 16, 1999.

BACKGROUND OF THE INVENTION

1. Field of the Invention

The present invention relates to compounds that can be used to treat, prophylactically or otherwise, uncontrolled or abnormal proliferation of tissues. Specifically, the present invention relates to compounds that inhibit the farnesyl transferase enzyme, which has been determined to activate ras proteins that in turn activate cellular division and are implicated in cancer, restenosis, and atherosclerosis.

2. Summary of the Related Art

Ras protein (or p21) has been examined extensively because mutant forms are found in 20% of most types of human cancer and greater than 50% of colon and pancreatic carcinomas (Gibbs J. B., Cell, 1991;65:1, Cartwright T. et al., Chimica. Oggi., 1992;10:26). These mutant ras proteins are deficient in the capability for feedback regulation that is present in native ras, and this deficiency is associated with their oncogenic action since the ability to stimulate normal cell division cannot be controlled by the normal endogenous regulatory cofactors. The recent discovery that the transforming activity of mutant ras is critically dependent on post-translational modifications (Gibbs J. et al., Microbiol. Rev., 1989;53:171) has unveiled an important aspect of ras function and identified novel prospects for cancer therapy.

In addition to cancer, there are other conditions of uncontrolled cellular proliferation that may be related to excessive expression and/or function of native ras proteins. Post-surgical vascular restenosis and atherosclerosis are such conditions. The use of various surgical revascularization techniques such as saphenous vein bypass grafting, endarterectomy, and transluminal coronary angioplasty are often accompanied by complications due to uncontrolled growth of neointimal tissue, known as restenosis. The biochemical causes of restenosis are poorly understood and numerous growth factors and protooncogenes have been implicated (Naftilan A. J. et al., Hypertension, 1989;13:706 and J. Clin. Invest., 83:1419; Gibbons G. H. et al., Hypertension, 1989;14:358; Satoh T. et al., Molec. Cell. Biol., 1993;13:3706). The fact that ras proteins are known to be involved in cell division processes makes them a candidate for intervention in many situations where cells are dividing uncontrollably. In direct analogy to the inhibition of mutant ras related cancer, blockade of ras dependent processes has the potential to reduce or eliminate the inappropriate tissue proliferation associated with restenosis or atherosclerosis, particularly in those instances where normal ras expression and/or function is exaggerated by growth stimulatory factors. See, for example, Kohl et al., Nature Med., 1995;1(8):792–748.

Ras functioning is dependent upon the modification of the proteins in order to associate with the inner face of plasma membranes. Unlike other membrane-associated proteins, ras proteins lack conventional transmembrane or hydrophobic sequences and are initially synthesized in a cytosol soluble form. Ras protein membrane association is triggered by a series of post-translational processing steps that are signaled by a carboxyl terminal amino acid consensus sequence that is recognized by protein farnesyl transferase (PFT). This consensus sequence consists of a cysteine residue located four amino acids from the carboxyl terminus, followed by two lipophilic amino acids, and the C-termninal residue. The sulfhydryl group of the cysteine residue is alkylated by farnesyl pyrophosphate in a reaction that is catalyzed by protein farnesyl transferase. Following prenylation, the C-terminal three amino acids are cleaved by an endoprotease and the newly exposed alpha-carboxyl group of the prenylated cysteine is methylated by a methyl transferase.

The enzymatic processing of ras proteins that begins with farnesylation enables the protein to associate with the cell membrane. Mutational analysis of oncogenic ras proteins indicate that these post-translational modifications are essential for transforming activity. Replacement of the consensus sequence cysteine residue with other amino acids gives a ras protein that is no longer farnesylated, fails to migrate to the cell membrane, and lacks the ability to stimulate cell proliferation (Hancock J. F. et al., Cell, 1989;57:1617; Schafer W. R. et al., Science, 1989;245:379; Casey P. J., Proc. Natl. Acad. Sci. USA, 1989;86:8323).

Recently, protein farnesyl transferases (PFTs), also referred to as farnesyl protein transferases (FPTs), have been identified and a specific PFT from rat brain was purified to homogeneity (Reiss Y. et al., Bioch. Soc. Trans., 1992;20:487–88). The enzyme was characterized as a heterodimer composed of one alpha-subunit (49 kDa) and one beta-subunit (46 kDa), both of which are required for catalytic activity. High expression levels of mammalian PFT in a baculovirus system and purification of the recombinant enzyme in active form has also been accomplished (Chen W.-J. et al., J. Biol. Chem., 1993;268:9675).

In light of the foregoing, the discovery that the function of oncogenic ras proteins is critically dependent on their post-translational processing provides a means of cancer chemotherapy through inhibition of the processing enzymes. The identification and isolation of a protein farnesyl transferase that catalyzes the addition of a farnesyl group to ras proteins provides a promising target for such intervention. Ras farnesyl transferase inhibitors have been shown to have anticancer activity in several recent articles.

Ras inhibitor agents act by inhibiting farnesyl transferase, the enzyme responsible for the post-translational modification of the ras protein which helps to anchor the protein product of the ras gene to the cell membrane. The role of the ras mutation in transducing growth signals within cancer cells relies on the protein being in the cell membrane. Inhibition of farnesyl transferase will result in the ras protein remaining in the cytosol and, consequently, being unable to transmit growth signals. These facts are well-known in the literature.

A peptidomimetic inhibitor of farnesyl transferase B956 and its methyl ester B1086 at 100 mg/kg have been shown to inhibit tumor growth by EJ-1 human bladder carcinoma, HT1080 human fibrosarcoma, and human colon carcinoma xenografts in nude mice (Nagasu T. et al., Cancer Res., 1995;55:5310–5314). Furthermore, inhibition of tumor growth by B956 has been shown to correlate with inhibition of ras post-translational processing in the tumor. Other ras farnesyl transferase inhibitors have been shown to specifically prevent ras processing and membrane localization and are effective in reversing the transformed phenotype of mutant ras containing cells (Sepp-Lorenzino L. et al., Cancer Res., 1995;55:5302–5309).

In another report (Sun J. et al., *Cancer Res.*, 1995;55:4243–4247), a ras farnesyl transferase inhibitor FT1276 has been shown to selectively block tumor growth in nude mice of a human lung carcinoma with K-ras mutation and p53 deletion. In yet another report, daily administration of a ras farnesyl transferase inhibitor L-744,832 caused tumor regression of mammary and salivary carcinomas in ras transgenic mice (Kohl et al., *Nature Med.*, 1995;1(8):792–748). Thus, ras farnesyl transferase inhibitors have benefit in certain forms of cancer, particularly those dependent on oncogenic ras for their growth.

It is well-known, however, that human cancer is often manifested when several mutations in important genes occurs, one or more of which mutations may be responsible for controlling growth and metastases. A single mutation may not be enough to sustain growth but after the occurrence of only two of three mutations, tumors can develop and grow. It is difficult, therefore, to determine which of these mutations may be primarily driving the growth in a particular type of cancer. Thus, ras farnesyl transferase inhibitors can have therapeutic utility in tumors not solely dependent on oncogenic forms of ras for their growth. For example, it has been shown that various ras FT-inhibitors have antiproliferative effects in vivo against tumor lines with either wild-type or mutant ras (Sepp-Lorenzino, supra.). In addition, there are several ras-related proteins that are prenylated. Proteins such as R-Ras2/TC21 are ras-related proteins that are prenylated in vivo by both farnesyl transferase and geranylgeranyl transferase I (Carboni et al., *Oncogene*, 1995;10:1905–1913). Therefore, ras farnesyl transferase inhibitors could also block the prenylation of the above proteins and, therefore, would then be useful in inhibiting the growth of tumors driven by other oncogenes.

With regard to the restenosis and vascular proliferative diseases, it has been shown that inhibition of cellular ras prevents smooth muscle proliferation after vascular injury in vivo (Indolfi C. et al., *Nature Med.*, 1995;1(6):541–545). This report definitively supports a role for farnesyl transferase inhibitors in this disease, showing inhibition of accumulation and proliferation of vascular smooth muscle.

A number of farnesyl transferase inhibiting compounds have been disclosed. WO 97/16443 and WO 97/21701 teach imidazolylmethyl 2-quinoline compounds of core structure:

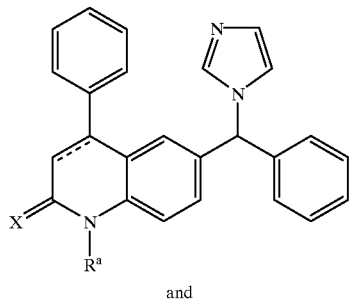

and

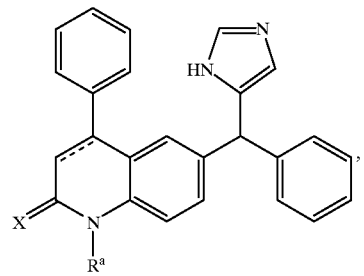

respectively, wherein each of the rings (other than the nitrogen containing ring) is optionally substituted. WO 98/40383 teaches 1,8-annelated quinolinone derivatives with N- or C-linked imidazoles of formula:

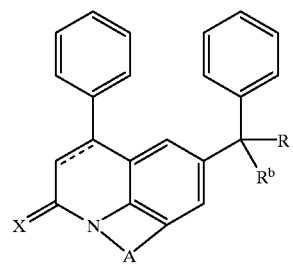

wherein $R^b$ is imidazolyl and A is a bivalent radical.

U.S. Pat. No. 4,690,932 teaches coumarin compounds for inhibiting platelet aggregation of formula A:

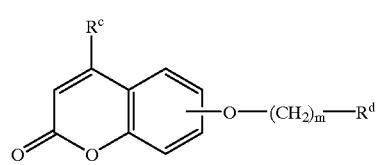

wherein $R^d$ is an imidazolyl or pyridyloxy group, $R^c$ is H or lower alkyl, and m is 1 to 6. Abyshev et al., *Pharm. Chem. J.*, 1993; 27:766 and Abyshev et al., *Khim-Farm. Zh.*, 1996;30:17–19 teach a compound of formula A in which $R^c$ is methyl or hydrogen, m is 2, and $R^d$ is imidazol-1-yl.

SUMMARY OF THE INVENTION

The present invention provides ras farnesyl transferase inhibiting 5 compounds having the Formula I:

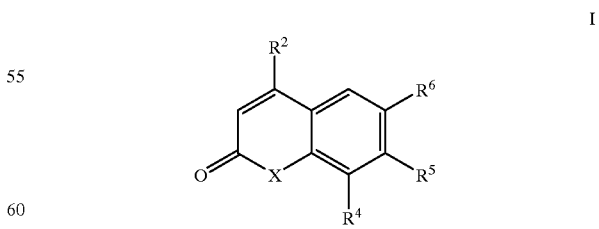

and the pharmaceutically acceptable salts thereof, wherein
X is —N—$R^3$ or O;
$R^2$ is alkyl, alkenyl, aryl, substituted aryl, aralkyl, substituted aralkyl, heteroaryl, substituted heteroaryl, heteroaralkyl, or substituted heteroaralkyl;

$R^3$ is hydrogen, alkyl, alkenyl, aralkyl, substituted aralkyl, aryl, or substituted aryl;

$R^4$ is hydrogen, alkyl, alkenyl, aryl, substituted aryl, aralkyl, substituted aralkyl, heteroaralkyl, or substituted heteroaralkyl;

one of $R^5$ and $R^6$ is hydrogen, and the other is —O—$R^1$;

$R^1$ is

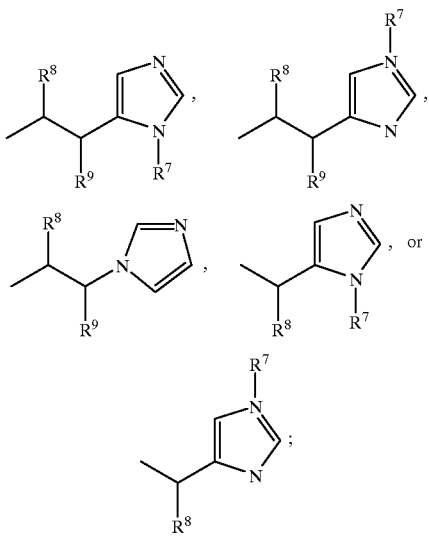

$R^7$ is hydrogen, alkyl, aralkyl, or substituted aralkyl; and $R^8$ and $R^9$ are independently hydrogen, alkyl, aryl, substituted aryl, heteroaryl, substituted heteroaryl, aralkyl, or substituted aralkyl;

provided, however, that when $R^2$ is hydrogen or $C_1$–$C_6$ alkyl, X is O, $R^4$ is hydrogen, $R^5$ or $R^6$ is —O—$R^1$, and $R^1$ is

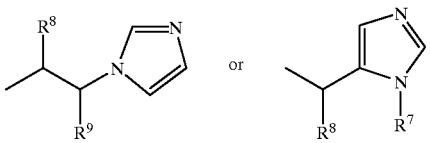

then, $R^7$, $R^8$, and $R^9$ are not all hydrogen.

In a preferred embodiment of the compounds of Formula I, X is O or —N—CH$_3$.

In another preferred embodiment of the compounds of Formula I, $R^2$ is chlorophenyl, phenyl, or methylphenyl.

In another preferred embodiment of the compounds of Formula I, $R^4$ is hydrogen, alkyl, alkenyl, aralkyl, or heteroarylalkyl.

In another preferred embodiment of the compounds of Formula I, $R^8$ is phenyl, and $R^9$ is hydrogen.

In another preferred embodiment of the compounds of Formula I, $R^7$ is hydrogen, benzyl, or methyl.

In a more preferred embodiment of the compounds of Formula I, $R^2$ is chlorophenyl, phenyl, or methylphenyl; and $R^4$ is hydrogen, alkyl, alkenyl, aralkyl, or heteroarylalkyl.

In a most preferred embodiment the compounds of Formula I are:

4-(3-Chloro-phenyl)-6-(2-imidazol-1-yl-1-phenyl-ethoxy)-1-methyl-8-propyl-1H-quinolin-2-one;

4-(3-Chloro-phenyl)-6-(2-imidazol-1-yl-1-phenyl-ethoxy)-1-methyl-8-phenethyl-1H-quinolin-2-one;

6-[2-(3-Benzyl-3H-imidazol-4-yl)-ethoxy]-4-(3-chloro-phenyl)-1-methyl-1H-quinolin-2-one;

6-[2-(3-Benzyl-3H-imidazol-4-yl)-ethoxy]-4-(3-chloro-phenyl)-1-methyl-8-propyl-1H-quinolin-2-one;

6-[2-(3-Benzyl-3H-imidazol-4-yl)-ethoxy]-4-(3-chloro-phenyl)-1-methyl-8-phenethyl-1H-quinolin-2-one;

4-(3-Chloro-phenyl)-7-(2-imidazol-1-yl-1-phenyl-ethoxy)-1-methyl-8-propyl-1H-quinolin-2-one;

4-(3-Chloro-phenyl)-7-(2-imidazol-1-yl-1-phenyl-ethoxy)-1-methyl-8-phenethyl-1H-quinolin-2-one;

7-[2-(3-Benzyl-3H-imidazol-4-yl)-ethoxy]-4-(3-chloro-phenyl)-1-methyl-1H-quinolin-2-one;

7-[2-(3-Benzyl-3H-imidazol-4-yl)-ethoxy]-4-(3-chloro-phenyl)-1-methyl-8-propyl-1H-quinolin-2-one;

7-[2-(3-Benzyl-3H-imidazol-4-yl)-ethoxy]-4-(3-chloro-phenyl)-1-methyl-8-phenethyl-1H-quinolin-2-one;

4-(2-Chloro-phenyl)-7-(2-imidazol-1-yl-1-phenyl-ethoxy)-8-propyl-chromen-2-one;

4-(2-Chloro-phenyl)-7-(2-imidazol-1-yl-1-phenyl-ethoxy)-8-phenethyl-chromen-2-one;

7-[2-(3-Benzyl-3H-imidazol-4-yl)-ethoxy]-4-(2-chloro-phenyl)-chromen-2-one;

7-[2-(3-Benzyl-3H-imidazol-4-yl)-ethoxy]-4-(2-chloro-phenyl)-8-propyl-chromen-2-one; and 7-[2-(3-Benzyl-3H-imidazol-4-yl)-ethoxy]-4-(2-chloro-phenyl)-8-phenethyl-chromen-2-one.

The present invention also provides a pharmaceutically acceptable composition that comprises a compound of Formula I.

The present invention also provides methods for inhibiting ras farnesyl transferase, the method comprising contacting ras farnesyl transferase with a compound according to the invention.

The present invention also provides a method of treating or preventing restenosis, the method comprising administering to a patient having restenosis or at risk of having restenosis a therapeutically effective amount of Formula I.

The present invention also provides a method of treating cancer, the method comprising administering to a patient having cancer a therapeutically effective amount of a compound of Formula I. In a preferred embodiment of the method of treating cancer, the cancer is lung, colon, pancreatic, thyroid, or bladder cancer.

The present invention also provides a method of treating atherosclerosis, the method comprising administering to a patient having atherosclerosis a therapeutically effective amount of a compound of Formula I.

In addition to the foregoing utilities, the ras farnesyl transferase inhibiting compounds of the invention are useful scientific research tools for in vitro investigations of the role of the ras protein in biological.

The foregoing merely summarizes certain aspects of the invention and is not intended, nor should it be construed, as limiting the invention in any manner. All patents, applications, and other publications cited herein are hereby incorporated by reference in their entirety.

DETAILED DESCRIPTION OF THE INVENTION

The present invention provides ras farnesyl transferase inhibiting compounds having the Formula I:

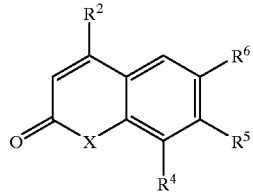

and the pharmaceutically acceptable salts thereof, wherein

X is —N—$R^3$ or O;

$R^2$ is alkyl, alkenyl, aryl, substituted aryl, aralkyl, substituted aralkyl, heteroaryl, substituted heteroaryl, heteroaralkyl, or substituted heteroaralkyl;

$R^3$ is hydrogen, alkyl, alkenyl, aralkyl, substituted aralkyl, aryl, or substituted aryl;

$R^4$ is hydrogen, alkyl, alkenyl, aryl, substituted aryl, aralkyl, substituted aralkyl, heteroarylalkyl, or substituted heteroarylalkyl;

one of $R^5$ and $R^6$ is hydrogen and the other is —O—$R^1$;

$R^1$ is

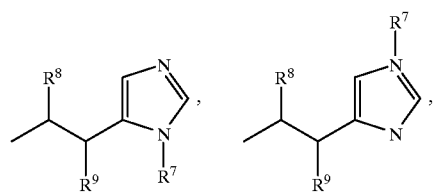

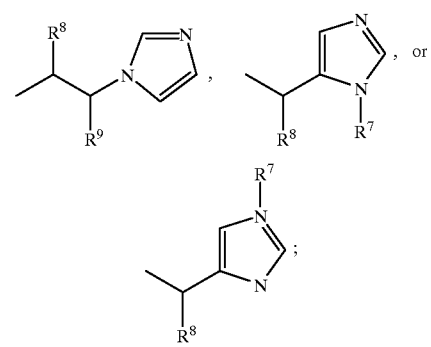

$R^7$ is hydrogen, alkyl, aralkyl or substituted aralkyl; and
$R^8$ and $R^9$ are independently hydrogen, alkyl, aryl, substituted aryl, heteroaryl, substituted heteroaryl, aralkyl, or substituted aralkyl;

provided, however, that when $R^2$ is hydrogen or $C_1$–$C_6$ alkyl, X is O, $R^4$ is hydrogen, $R^5$ or $R^6$ is —O—$R^1$, and $R^1$ is

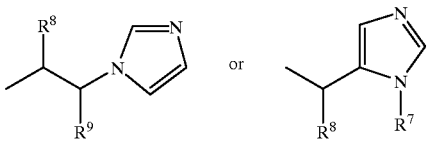

then, $R^7$, $R^8$, and $R^9$ are not all hydrogen.

Preferred compounds of the invention are:

4-(3-Chloro-phenyl)-6-(2-imidazol-1-yl-1-phenyl-ethoxy)-1-methyl-8-propyl-1H-quinolin-2-one:

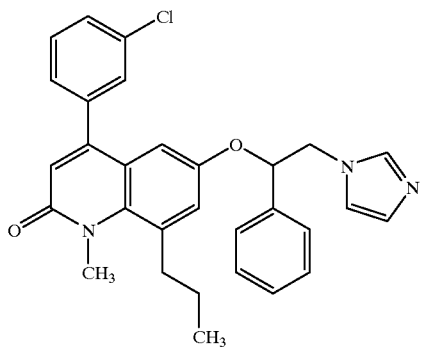

4-(3-Chloro-phenyl)-6-(2-imidazol-1-yl-1-phenyl-ethoxy)-1-methyl-8-phenethyl-1H-quinolin-2-one:

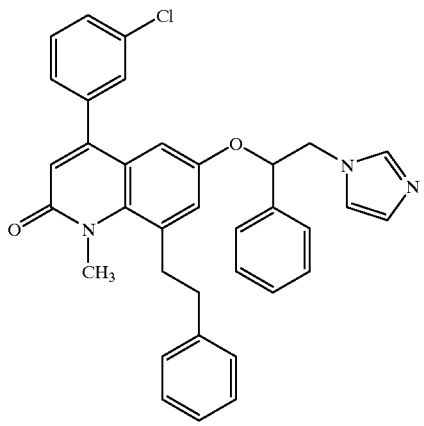

6-[2-(3-Benzyl-3H-imidazol-4-yl)-ethoxy]-4-(3-chloro-phenyl)-1-methyl-1H-quinolin-2-one:

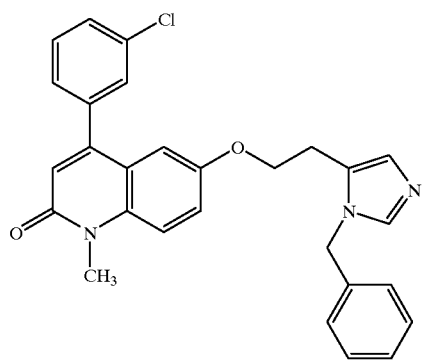
6-[2-(3-Benzyl-3H-imidazol-4-yl)-ethoxy]-4-(3-chloro-phenyl)-1-methyl-8-propyl-1H-quinolin-2-one:
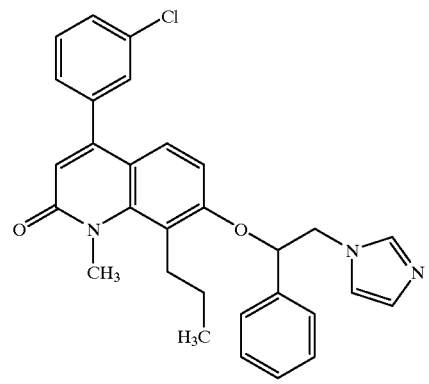
4-(3-Chloro-phenyl)-7-(2-imidazol-1-yl-1-phenyl-ethoxy)-1-methyl-8-phenethyl-1H-quinolin-2-one:
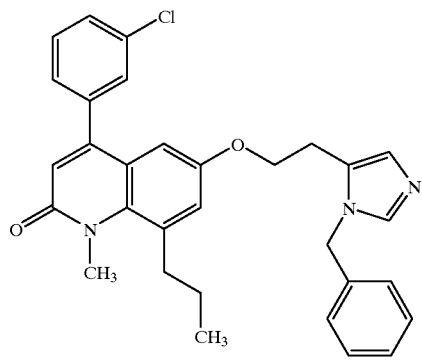
6-[2-(3-Benzyl-3H-imidazol-4-yl)-ethoxy]-4-(3-chloro-phenyl)-1-methyl-8-phenethyl-1H-quinolin-2-one:
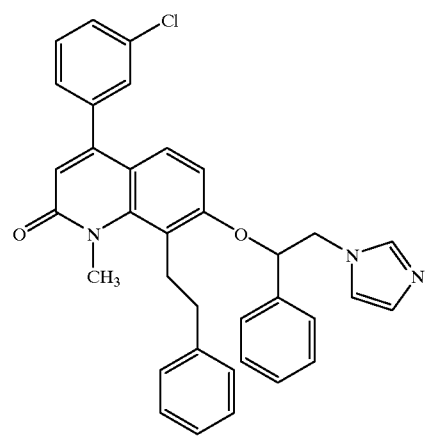
7-[2-(3-Benzyl-3H-imidazol-4-yl)-ethoxy]-4-(3-chloro-phenyl)-1-methyl-1H-quinolin-2-one:
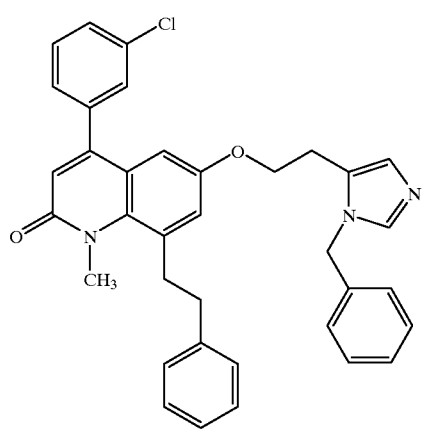
4-(3-Chloro-phenyl)-7-(2-imidazol-1-yl-1-phenyl-ethoxy)-1-methyl-8-propyl-1H-quinolin-2-one:
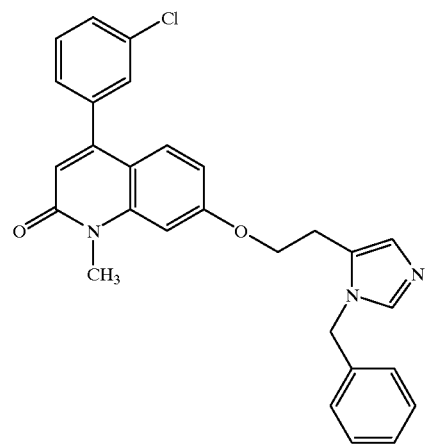

7-[2-(3-Benzyl-3H-imidazol-4-yl)-ethoxy]-4-(3-chloro-phenyl)-1-methyl-8-propyl-1H-quinolin-2-one:

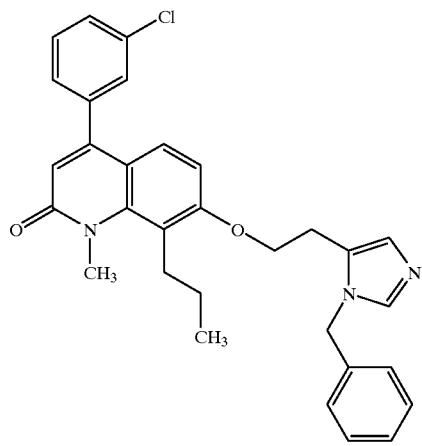

7-[2-(3-Benzyl-3H-imidazol-4-yl)-ethoxy]-4-(3-chloro-phenyl)-1-methyl-8-phenethyl-1H-quinolin-2-one:

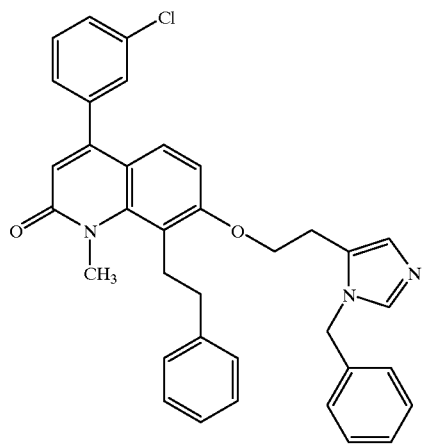

4-(2-Chloro-phenyl)-7-(2-imidazol-1-yl-1-phenyl-ethoxy)-8-propyl-chromen-2-one:

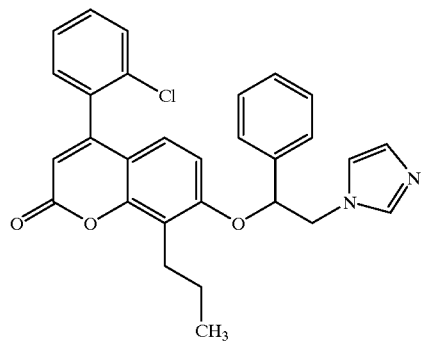

4-(2-Chloro-phenyl)-7-(2-imidazol-1-yl-1-phenyl-ethoxy)-8-phenethyl-chromen-2-one:

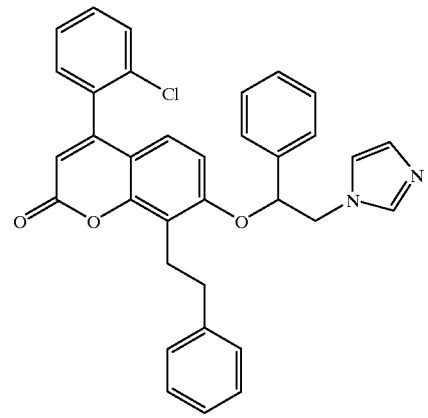

7-[2-(3-Benzyl-3H-imidazol-4-yl)-ethoxy]-4-(2-chloro-phenyl)-chromen-2-one:

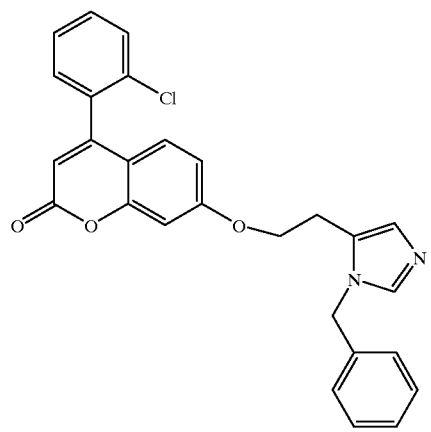

7-[2-(3-Benzyl-3H-imidazol-4-yl)-ethoxy]-4-(2-chloro-phenyl)-8-propyl-chromen-2-one:

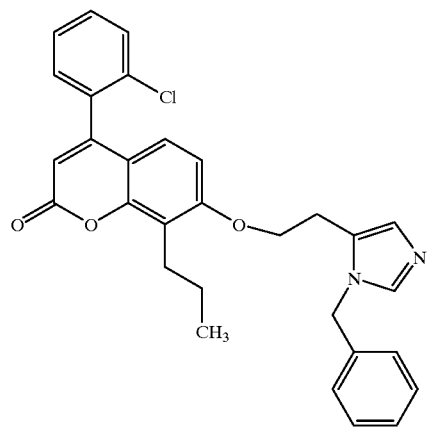

7-[2-(3-Benzyl-3H-imidazol-4-yl)-ethoxy]-4-(2-chloro-phenyl)-8-phenethyl-chromen-2-one:

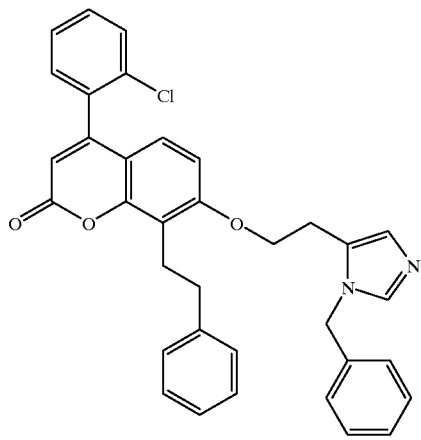

The term "alkyl" means a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents listed below. Preferred alkyl groups are $C_1$–$C_6$ alkyl.

The term "cycloalkyl" means a saturated hydrocarbon ring which contains from 3 to 7 carbon atoms, for example, cyclopropyl, cyclobutyl, cyclopentyl, cyclohexyl, and the like.

The term "aryl" means an aromatic ring such as phenyl, fluorenyl, or naphthyl.

The term "substituted" means that one or more hydrogen atom in a molecule has been replaced with another atom or group of atoms. For example, substituents include alkyl, O-alkyl, O-alkenyl, S-alkyl, OH, SH, F, —CN, Cl, Br, I, $CF_3$, $NO_2$, $NH_2$, NH(alkyl), N(alkyl)$_2$, NHCO-alkyl, —(CH$_2$)$_m$CO$_2$H, —(CH$_2$)$_m$CO$_2$-alkyl, —(CH$_2$)$_m$SO$_3$H, —(CH$_2$)$_m$PO$_3$H$_2$, —(CH$_2$)$_m$PO$_3$(alkyl)$_2$, —(CH$_2$)$_m$SO$_2$NH$_2$, and —(CH$_2$)$_m$SO$_2$NH-alkyl, wherein alkyl is defined as above and m is 0, 1, 2, or 3.

The term "aralkyl" means an alkyl group (as defined above) substituted with an aryl group (also as defined above). A preferred aralkyl is benzyl.

The term "heteroaryl" means an aromatic ring in which one or more carbon atom in the aromatic ring has been replaced with a heteroatom. Examples of heteroatoms include, nitrogen, oxygen, and sulfur.

The term "heteroaralkyl" means an alkyl group substituted with a heteroaryl group.

The term "alkenyl" means a hydrocarbon having one or more double bond.

The symbol "—" means a bond.

The term "patient" means all animals including humans. Examples of patients include humans, cows, dogs, cats, goats, sheep, and pigs.

A "therapeutically effective amount" is an amount of a compound of the present invention that when administered to a patient ameliorates a symptom of restenosis, cancer, or atherosclerosis or prevents restenosis. A therapeutically effective amount of a compound of the present invention can be easily determined by one skilled in the art by administering a quantity of a compound to a patient and observing the result. In addition, those skilled in the art are familiar with identifying patients having cancer, restenosis, or atherosclerosis or who are at risk of having restenosis.

The term "cancer" includes, but is not limited to, the following cancers: breast, ovary, cervix, prostate, testis, esophagus, glioblastoma, neuroblastoma, stomach, skin, keratoacanthoma, lung, epidermoid carcinoma, large cell carcinoma, adenocarcinoma, bone, colon, adenocarcinoma, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkins, hairy cells, buccal cavity and pharynx (oral), lip, tongue, mouth, pharynx, small intestine, colon-rectum, large intestine, rectum, brain and central nervous system; and leukemia. Preferred ras-related cancers to be treated by the compounds of the present invention include lung colon, pancreatic, thyroid, or bladder cancers.

The term pharmaceutically acceptable salts, esters, amides, or prodrugs means those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," J. Pharm. Sci., 1977;66:1–19 which is incorporated herein by reference.)

Examples of pharmaceutically acceptable, nontoxic esters of the compounds of this invention include $C_1$–$C_6$ alkyl esters wherein the alkyl group is a straight or branched chain. Acceptable esters also include $C_5$∫$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, nontoxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

Synthesis of the compounds of the invention can be conducted according to the following general synthetic procedures, with references to the Examples below. The appropriate hydroxychromenone or hydroxyquinolinone is dissolved or suspended in an inert solvent such as dioxane, toluene, dichloromethane or preferably tetrahydrofuran to which is added the selected imidazolemethanol or imidazoleethanol compound. To the mixture is added a coupling activation reagent preferably a combination of triphenylphosphine and diethyl azodicarboxylate. The mixture may be combined under an inert atmosphere at −40° C. to +35° C. and allowed to stir from 2 to 48 hours. The mixture may be evaporated to a residue and purified by partition between an inert solvent and water by adjustment of the pH of the solution, and/or by silica gel chromatography.

Administration of the compounds of the present invention can be alone to a patient or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well-known to those skilled in the art.

The compounds of the present invention can exist in different stereoisomeric forms by virtue of the presence of asymmetric centers in the compounds. It is contemplated that all stereoisomeric forms of the compounds as well as mixtures thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The examples presented below are intended to illustrate particular embodiments of the invention, and are not intended to limit the scope of the specification or the claims in any way.

The following abbreviations are used in the application.

| | |
|---|---|
| HPLC | High pressure liquid chromatography |
| CI-MS | Chemical Ionization Mass Spectrometry |
| mp | Melting point |
| rt | Room temperature |
| THF | Tetrahydrofuran |
| APCI-MS | Atmospheric pressure chemical ionization mass spectrometry |
| dec | Decomposes |
| AcCN | Acetonitrile |
| HOAc | Acetic acid |
| DCM | Dichloromethane |
| DMF | N,N'-Dimethylformamide |
| EtOAc | Ethyl acetate |
| EtOH | Ethanol |
| $Et_2O$ | Diethyl ether |
| MeCN | Acetonitrile |
| MeOH | Methanol |
| iPrOH | iso-Propanol |
| TFA | Trifluoroacetic acid |
| Boc | tertiary Butyloxycarbonyl |
| Ts | Tosylate |
| $Ph_3P$ | Triphenylphosphine |
| nBuLi | n-Butyl lithium |
| DEAD | Diethyl azodicarboylate |
| Con. | Concentrated |

Melting points are uncorrected. Proton NMR ($^1$H-NMR) spectra were obtained at 300 or 400 MHz and are reported relative to tetramethylsilane (TMS). When indicated, analytical HPLC was performed on Vydac C18 peptide/protein or Beckman Ultrasphere ODS C18 columns eluting with gradients of water/acetonitrile containing 0.1% TFA. Flash chromatography was performed using Merck or ICN silica gel, 60A, 230–400 mesh. THF was distilled from Na/benzophenone, and all other solvents were reagent grade.

EXAMPLES

Compounds of the present invention can be generally prepared as follows:

The appropriate hydroxychromenone or hydroxyquinolinone is dissolved or suspended in an inert solvent such as dioxane, toluene, dichloromethane, or preferably tetrahydrofuran to which is added the selected imidazolemethanol or imidazoleethanol compound. To the mixture is added a coupling activation reagent, preferably a combination of triphenylphosphine and diethyl azodicarboylate. The mixture may be combined under an inert atmosphere at −40° C. to +35° C. and allowed to stir from 2 to 48 hours. The mixture may be evaporated to a residue and purified by partitioning between an inert solvent and water by adjustment of the pH of the solution, crystallization, and/or by silica gel chromatography.

Example 1

Synthesis of 4-(3-Chloro-phenyl)-6-(2-imidazol-1-yl-1-phenyl-ethoxy)-1-methyl-1H-quinolin-2-one

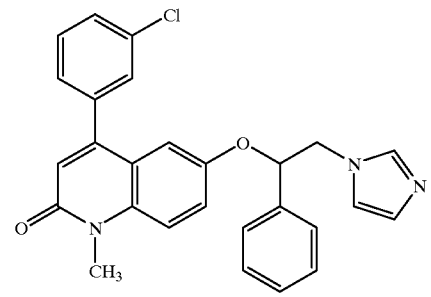

1a. Synthesis of N-(4-Methoxy-phenyl)-N-methyl-malonamic acid methyl ester

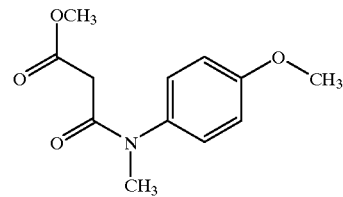

To dichloromethane (800 mL) was added N-methyl-p-anisidine (36 g, 0.262 mol, Aldrich Chemical Corp., Milwaukee, Wis.) and triethylamine (39.5 mL, 0.283 mol). A solution of methyl malonyl chloride (38.7 g, 0.283 mol) in dichloromethane (50 mL) was then gradually added. The mixture exothermed to reflux. After 1 hour, the solvent was removed in vacuo, the residue was taken up into ethyl ether and washed consecutively with 1N citric acid and brine. The organic phase was dried over anhydrous magnesium sulfate, filtered, and evaporated in vacuo to an oil, 62.4 g, 100% yield. NMR was consistent with structure. MS: APCI: M+1: 238.1 (M: 237.3).

1b. Synthesis of N-(4-methoxy-phenyl)-N-methyl-malonamic acid

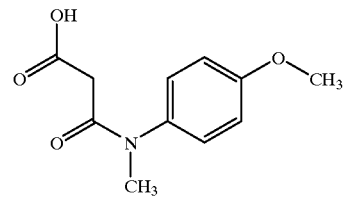

N-(4-methoxy-phenyl)-N-methyl-malonamic acid methyl ester (52.2 g, 0.22 mol) was dissolved in methanol (250 mL) to which 1N NaOH (250 mL) was added. After stirring at 25° C. for 2.5 hours, the methanol was evaporated in vacuo, and the residue was washed with ethyl ether. The aqueous phase was acidified to Congo red by addition of conc. HCl and extracted into ethyl acetate. The organic extract was washed with brine, dried over anhydrous magnesium sulfate, filtered, and evaporated to an oil. The oil was crystallized from a solution of ethyl ether and pentane, dried in vacuo giving a white solid, 39.9 g, 81% yield, mp 85–87° C., NMR was consistent with structure. MS: APCI: M+1: 224.1 (M: 223.2).

1c. Synthesis of 4-Hydroxy-6-methoxy-1-methyl-1H-quinolin-2-one

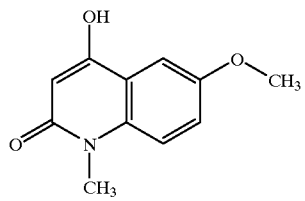

N-(4-Methoxy-phenyl)-N-methyl-malonamic acid, (39.75 g, 0.178 mol)) was suspended in polyphosphoric acid (450 g) and heated to 150° C. over 30 minutes and held at that temperature for 15 minutes. The mixture was cooled to 90° C., and the resulting oil was poured with vigorous stirring into water (450 mL). Ice was added to cool the resulting suspension to 10° C., and it was filtered. The collected solid was repeatedly washed with water and dried by suction to a damp cake. The solid was taken up into warm chloroform/methanol (85:15), the phases separated, the organic phase dried over anhydrous magnesium sulfate, filtered, and evaporated in vacuo giving a solid precipitate. The solid was filtered and dried in vacuo to a solid, 22.08 g, 65% yield, mp 274–277° C. NMR was consistent with structure. MS: APCI: M+1: 206.1 (M: 205.2).

1d. Synthesis of Trifluoro-methanesulfonic acid 6-methoxy-1-methyl-2-oxo-1,2-dihydro-quinolin-4-yl ester

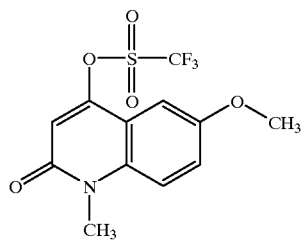

4-Hydroxy-6-methoxy-1-methyl-1H-quinolin-2-one, (21.3 g, 0.112 mol) was suspended in a mixture of dichloromethane (750 mL) and pyridine (70 mL). To this was added a solution of trifluoromethane sulfonic anhydride (23 mL, 0.134 mol) in dichloromethane (50 mL) over 10 minutes, giving an exotherm and complete solution. After stirring 2 hours at 25° C., the mixture was washed repeatedly with 1N citric acid, saturated sodium bicarbonate solution, and brine. The organic phase was dried over anhydrous magnesium sulfate, filtered, and evaporated in vacuo to small volume to which ethyl ether and pentane were added to give a crystalline solid. The suspension was filtered and the solid dried in vacuo giving a yellow solid, 25 g, 66% yield. NMR was consistent with structure. MS: APCI: M+1: 338 (M: 337.3).

1e. Synthesis of 4-(3-Chloro-phenyl)-6-methoxy-1-methyl-1H-quinolin-2-one

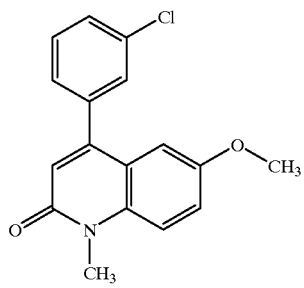

To 500 mL dry distilled tetrahydrofuran was added 3-bromochlorobenzene (24.6 g, 0.129 mol) followed by cooling to −72° C. Over 10 minutes was added a solution of n-BuLi in hexanes (1.6 M, 80.5 mL), followed by stirring at −72° C. for 45 minutes. A solution of anhydrous zinc bromide (29 g, 0.129 mol) in 135 mL dry tetrahydrofuran was added over 20 minutes, followed by warming to 25° C. over 45 minutes. To this solution, as a mixture of solids was added trifluoro-methanesulfonic acid 6-methoxy-1-methyl-2-oxo-1,2-dihydro-quinolin-4-yl ester, (25.7 g, 0.076 mol) and palladium tetrakis(triphenylphosphine) (11.7 g, 0.01 mol), giving a dark solution. After 2 hours, the solvent was evaporated in vacuo, and the residue was diluted with ethyl acetate. A solid precipitate of spent catalyst was filtered off, and the filtrate was washed with 1N citric acid, saturated sodium bicarbonate, and brine. The organic phase was dried over anhydrous magnesium sulfate, filtered, and evaporated while cold to a small volume giving a crystalline solid. The solid was filtered, washed with ethyl ether, and dried in vacuo giving a solid, mp 126–129° C., 14.26 g, 55% yield. NMR was consistent with structure. MS: APCI: M+1: 300.0 (M: 299.7).

1f. Synthesis of 4-(3-Chloro-phenyl)-6-hydroxy-1-methyl-1H-quinolin-2-one

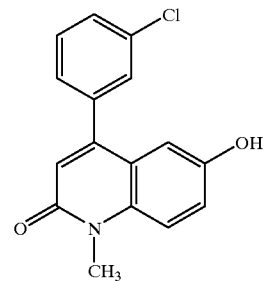

To 130 mL 47% HBr was added 4-(3-chloro-phenyl)-6-methoxy-1-methyl-1H-quinolin-2-one (13.0 g, 0.0434 mol). The mixture was heated to 140° C. overnight. The resulting slurry was filtered while hot, washed with 45% HBr and water. The solid was dried under vacuum at 60° C. giving a yellow solid, 14 g, mp 230–235° C. NMR was consistent with structure. MS: APCI: M+1: 286.0 (M: 285.7). The material was sufficiently pure for use in the following step.

1g. Synthesis of 2-Imidazol-1-yl-phenyl-ethanol

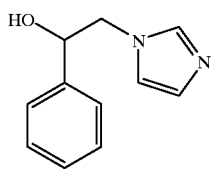

To absolute ethanol (100 mL) was added imidazole (17.6 g, 0.258 mol) and pyridine (0.6 mL). The mixture was heated to reflux for 25 minutes. A solution of styrene oxide (31.06 g, 0.258 mol) in ethanol (40 mL) was added dropwise. The mixture was refluxed overnight. The mixture was evaporated to a syrup and partitioned between ethyl ether and water. Agitation of the mixture gave a solid which was filtered and washed with water and ethyl ether. The solid was dissolved in a mixture of hot ethyl acetate and chloroform (30:70). The solution was filtered, washed with brine and dried over anhydrous magnesium sulfate and charcoal. The suspension was filtered, concentrated in vacuo giving a solid. The solid was washed with ethyl ether and dried in vacuo giving 17.09 g of a white solid, 35% yield, mp 146–148° C. NMR was consistent with structure. MS: APCI: M+1: 189.2 (M: 188.2).

1h. Synthesis of 4-(3-Chloro-phenyl)-6-(2-imidazol-1-yl-1-phenyl-ethoxy)-1-methyl-1H-quinolin-2-one

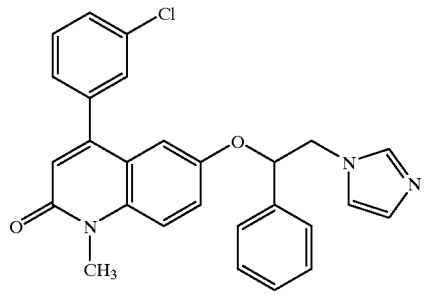

To 250 mL of dry tetrahydrofuran was added 4-(3-chloro-phenyl)-6-hydroxy-1-methyl-1H-quinolin-2-one (1.71 g, 6.0 mmol), 2-imidazol-1-yl-phenyl-ethanol, (1.31 g, 7.0 mmol) and triphenylphosphine (1.84 g, 7.0 mmol). To the mixture was added a solution of diethyl azodicarboxylate (1.22 g, 7.0 mmol) in tetrahydrofuran (20 mL). The mixture was stirred at 25° C. overnight and evaporated in vacuo. The residue was taken up into ethyl ether and extracted with 1N citric acid. The ether phase was discarded, and the pH of the aqueous phase was adjusted to 7.5 by addition of 4N NaOH. The solution was extracted with ethyl ether, washed with brine, dried over anhydrous magnesium sulfate, and filtered. The solution was evaporated in vacuo to a foam, 1.26 g. The foam was repeatedly purified by silica gel chromatography, eluted with a gradient of 0% to 5% methanol in chloroform. The product was recovered as a foam, 0.34 g, 12% yield. NMR was consistent with structure. MS: APCI: M+1: 456.1 (M: 455.7).

Analysis calculated for $C_{27}H_{22}N_3O_2Cl0.5\ H_2O$: C, 68.99; H, 4.93; N, 8.85; $H_2O$, 1.91. Found: C, 69.17; H, 4.79; N, 9.13; $H_2O$, 1.94.

Example 2

Synthesis of 4-(3-Chloro-phenyl)-7-(2-imidazol-1-yl-1-phenyl-ethoxy)-1-methyl-1H-quinolin-2-one

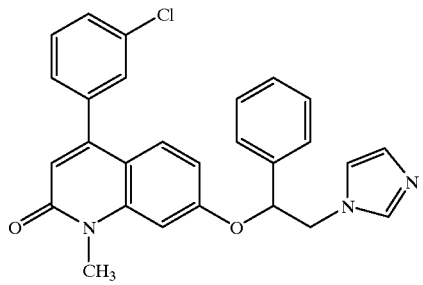

2a. Synthesis of (N-Methyl-m-anisidine)

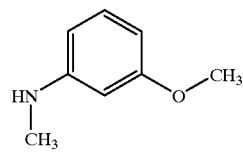

m-Anisidine (Aldrich Chemical Corp.) was substituted for p-anisidine in the procedure described in Journal Chemical Society, London, 1969:2223, Perkin Transactions I., which gave N-methyl-m-anisidine, as an oil, 24.5 g, 77% yield. NMR was consistent with structure. MS: APCI: M+1: 138.2 (M: 137.2).

2b. Synthesis of N-(3-Methoxy-phenyl)-N-methyl-malonamic acid methyl ester

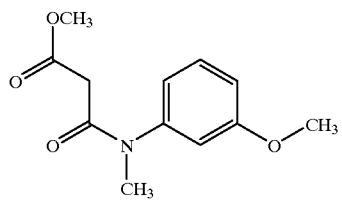

By a procedure similar to that of intermediate 1a, N-methyl-p-anisidine (24.3 g, 0.177 mol, Aldrich Chemical Corp.) gave an oil, 38.5 g, 91% yield. NMR was consistent with structure. MS: APCI: M+1: 238.1 (M: 237.3).

2c. Synthesis of N-(3-Methoxy-phenyl)-N-methyl-malonamic acid

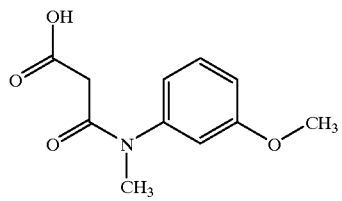

By a procedure similar to that of intermediate 1b, N-(3-methoxy-phenyl)-N-methyl-malonamic acid methyl ester (38.8 g, 0.164 mol) gave an oil, 31.43 g, 86% yield. NMR was consistent with structure. MS: APCI: M+1: 224.1 (M: 223.2).

2d. Synthesis of 4-Hydroxy-7-methoxy-1-methyl-1H-quinolin-2-one

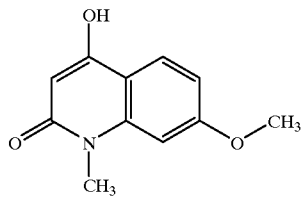

By a procedure similar to that of intermediate 1c, N-(3-methoxy-phenyl)-N-methyl-malonamic acid, (30.8 g, 0.138 mol) gave a solid. Recrystallization of the solid from hot ethyl acetate isolated the correct regioisomer as a solid 9.12 g, 38% yield. NMR was consistent with structure. MS: APCI: M+1: 206.1 (M: 205.2).

2e. Synthesis of Trifluoro-methanesulfonic acid 7-methoxy-1-methyl-2-oxo-1,2-dihydro-quinolin-4-yl ester

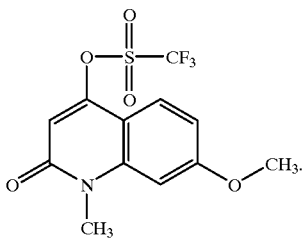

By a procedure similar to that of intermediate 1d, 4-hydroxy-7-methoxy-1-methyl-1H-quinolin-2-one (8.94 g, 0.0435 mol) gave a gummy solid to which ethyl ether was added to give a crystalline solid. The suspension was filtered and the solid dried in vacuo, 9.28 g, 63% yield. NMR was consistent with structure. MS: APCI: M+1: 338 (M: 337.3).

2f. Synthesis of 4-(3-Chloro-phenyl)-7-methoxy-1-methyl-1H-quinolin-2-one

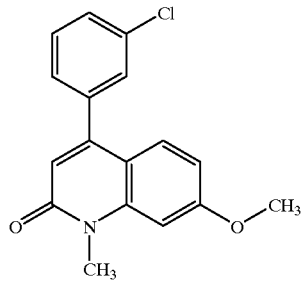

By a procedure similar to that of intermediate 1e, trifluoro-methanesulfonic acid 7-methoxy-1-methyl-2-oxo-1,2-dihydro-quinolin-4-yl ester (9.09 g, 0.027 mol) gave a crystalline solid, 8.09 g. The solid purified by chromatography on silica gel eluted with hexane/ethyl acetate (50:50), giving a solid, 5.4 g, 67% yield. NMR was consistent with structure. MS: APCI: M+1: 300.0 (M: 299.7).

2g. Synthesis of 4-(3-Chloro-phenyl)-7-hydroxy-1-methyl-1H-quinolin-2-one

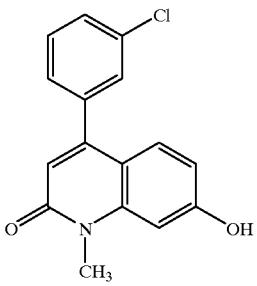

By a procedure similar to that of intermediate 1f, 4-(3-chloro-phenyl)-7-methoxy-1-methyl-1H-quinolin-2-one (5.2 g, 0.017 mol) gave a solid, 3.98 g, 80%. NMR was consistent with structure. MS: APCI: M+1: 286.0 (M: 285.7).

2h. Synthesis of 4-(3-Chloro-phenyl)-7-(2-imidazol-1-yl-1-phenyl-ethoxy)-1-methyl-1H-quinolin-2-one

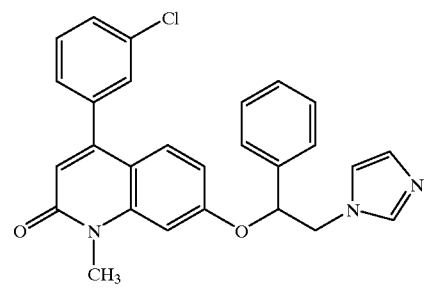

By a procedure similar to that of compound (1), 4-(3-chloro-phenyl)-7-hydroxy-1-methyl-1H-quinolin-2-one (1.71 g, 6.0 mmol) gave an oil, 2.20 g. The oil was purified by silica gel chromatography, eluted with a gradient of 0% to 4% methanol in chloroform. The product was recovered as a foam, 2.20 g, 81% yield. NMR was consistent with structure. MS: APCI: M+1: 456.1 (M: 455.7).

Analysis calculated for $C_{27}H_{22}N_3O_2Cl$, 0.1 $H_2O$, 0.1 $CHCl_3$: C, 69.30; H, 4.79; N, 8.95; $H_2O$, 3.84; Cl, 9.81. Found: C, 68.98; H, 4.82; N, 8.95; $H_2O$, 1.03; Cl, 9.15.

Example 3

Synthesis of 4-(3-Chloro-phenyl)-6-(1H-imidazol-4-ylmethoxy)-1-methyl-1H-quinolin-2-one

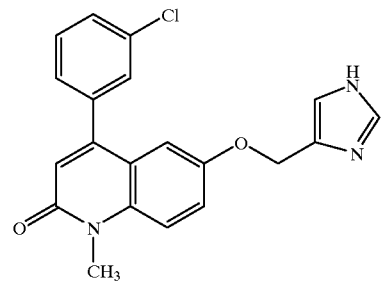

3a. Synthesis of (1-Trityl-1H-imidazol-4-yl)-methanol

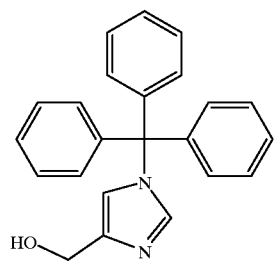

4-(Hydroxymethylmethyl)imidazole hydrochloride (4.66 g, 0.034 mol, Aldrich Chemical Corp.) was dissolved in dimethylformamide (30 mL). Triethylamine (11.6 mL, 0.0836 mol) was added, giving a white precipitate. A solution of trityl chloride (9.94 g, 0.0356 mol) in dimethylformamide (125 mL) was added, and the mixture was stirred for 1 hour. The suspension was filtered, washed with water, resuspended in water, and filtered. The solid was dried in vacuo at 60° C. giving a solid, 10.5 g, 91% yield, mp 198–202° C. NMR was consistent with structure.

3b. Synthesis of 4-(3-Chloro-phenyl)-1-methyl-6-(1-trityl-1H-imidazol-4-ylmethoxy)-1H-quinolin-2-one

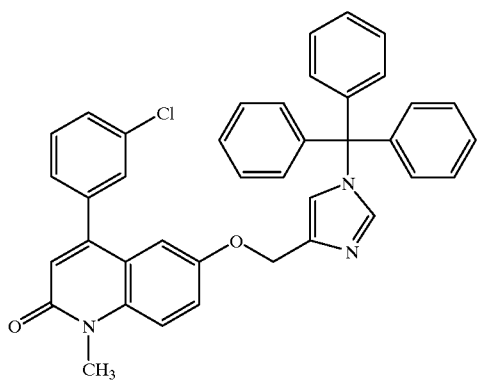

To dichloromethane was added (1-trityl-1H-imidazol-4-yl)-methanol (0.7 g, 2.05 mmol), 4-(3-chlorophenyl)-6-hydroxy-1-methyl-1H-quinolin-2-one (0.56 g, 1.96 mmol) and triphenylphosphine (0.56 g, 2.14 mmol) giving a suspension. To this was added tetrahydrofuran, 25 mL. A solution of diethyl azodicarbozylate (0.374 g, 2.14 mmol) in 20 mL tetrahydrofuran was added over 3 minutes. The mixture was stirred overnight at 25° C. The mixture was evaporated in vacuo, and the residue was taken up into ethyl ether and water, giving a suspended solid. The mixture was filtered and the solid dissolved in methylene dichloride. The solution was washed with brine, dried over anhydrous magnesium sulfate, filtered, and precipitated by addition of ethyl ether. The resulting solid was filtered and dried giving a solid, 0.339 g. The solid was chromatographed on 25 g silica gel which was eluted with chloroform. The product was recovered as a solid, 0.33 g, 28% yield, NMR was consistent with structure.

3c. Synthesis of 4-(3-Chloro-phenyl)-6-(1H-imidazol-4-ylmethoxy)-1-methyl-1H-quinolin-2-one

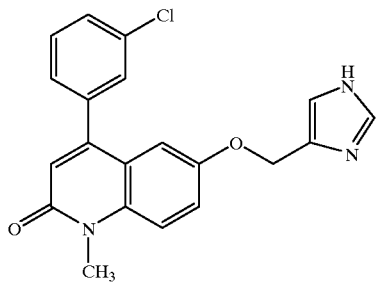

To 90% acetic acid was added 4-(3-chloro-phenyl)-1-methyl-6-(1-trityl-1H-imidazol-4-ylmethoxy)-1H-quinolin-2-one (0.33 g, 0.54 mmol) followed by heating on a steam bath for 15 minutes. After cooling to 25° C. for 1 hour, a solid precipitated. The solid was filtered, and the filtrate was evaporated in vacuo to a semi-solid, which upon trituration with a mixture of ethyl acetate/ethyl ether gave a solid. Upon drying in vacuo, there was obtained a solid, 0.169 g, 85% yield. NMR was consistent with structure. MS: APCI: M+1: 366.1 (M: 365.8).

Analysis calculated for $C_{20}H_{16}N_3O_2Cl$, 0.75 HOAc: C, 62.85; H, 4.66; N, 9.88; Cl, 8.33. Found: C, 62.89; H, 4.77; N, 10.62; Cl, 8.96.

Example 4

Synthesis of 4-(3-Chloro-phenyl)-1-methyl-6-[(3-methyl-3H-imidazol-4-yl)-phenyl-methoxy]-1H-quinolin-2-one

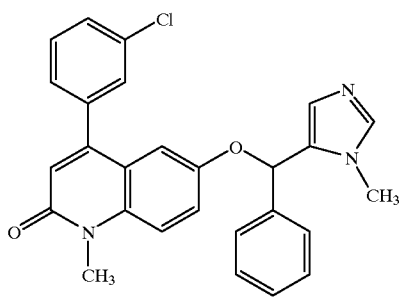

4a. Synthesis of 1-Trityl-1H-imidazole-4-carbaldehyde

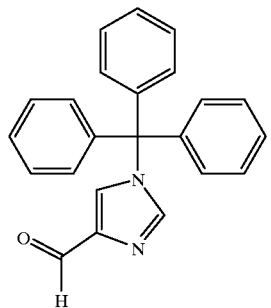

To dimethylformamide (100 mL) was added imidazole-4-carboxaldehyde (10 g, 0.104 mol, Aldrich Chemical Corp.) and triethylamine (20.5 mL, 0.147 mol). A solution of trityl chloride (40 g, 0.143 mol) in dimethylformamide (300 mL) was added, followed by stirring at 25° C. for 6 hours. The solvent was removed in vacuo, and the residue was dissolved in ethyl acetate (1.5 L) and 1N citric acid (350 mL). The phases were separated, and the organic phase was washed with brine, dried over anhydrous magnesium sulfate, and filtered. Concentration of the solution in vacuo gave a white solid, 27.59 g, 78% yield. NMR was consistent with structure. MS: APCI: M-1: 337.2 (M: 338.41).

4b. Synthesis of Phenyl-(1-trityl-1H-imidazol-4-yl)-methanol

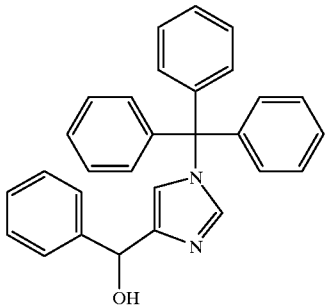

To tetrahydrofuran (400 mL) was added 1-trityl-1H-imidazole-4-carbaldehyde (20 g, 0.059 mol), followed by cooling to −78° C. A solution of phenyllithium (70 mL, 1.8 M in hexane) was added at −78° C. The mixture was warmed to 25° C. over 3.5 hours, followed by refrigeration at 5° C. overnight. Water was added to the mixture, followed by agitation and filtration of minor insolubles. The organic phase was washed with brine, dried over anhydrous magnesium sulfate, and filtered. Concentration of the solution in vacuo gave a crystalline solid, 18.77 g, 76% yield. NMR was consistent with structure.

4c. Synthesis of 5-(Hydroxy-phenyl-methyl)-1-methyl-3-trityl-3H-imidazol-1-ium Iodide

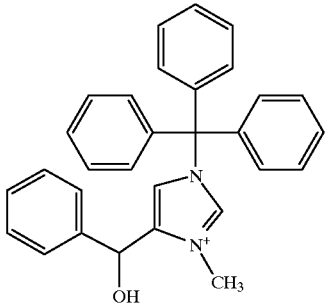

To dichloromethane (75 mL) was added phenyl-(1-trityl-1H-imidazol-4-yl)-methanol (6.0 g, 0.014 mol). Methyl iodide (30 mL) was added, and the mixture was capped and stirred at 25° C. overnight. The solution was evaporated in vacuo to an oil. The oil was diluted with dichloromethane, and an oil was precipitated from this solution by addition of ethyl ether. The solvents were decanted, leaving the oil behind to solidify. Additional crystallizations from dichloromethane and ethyl ether gave a solid, 4.41 g, 55% yield. MS: APCI: M+1: 189.1 (M-trityl: 188.23). The material was sufficiently pure for use in the subsequent reactions.

4d. Synthesis of (3-Methyl-1H-imidazol-4-yl)-phenyl-methanol

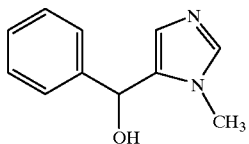

To 90% acetic acid (90 mL) was added 5-(hydroxy-phenyl-methyl)-1-methyl-3-trityl-3H-imidazol-1-ium iodide (6.0 g, 0.011 mol) and sodium acetate (1.0 g), followed by heating on a steam bath for 1 hour. The oily suspension was diluted with 30 mL water giving a solid precipitate. The solid was filtered, diluted with additional water, and the resulting solids filtered. The filtrate was evaporated in vacuo to a solid which was redissolved in water, treated with charcoal to remove color, and filtered through Celite. The filtrate was evaporated to a paste in vacuo. The paste was partitioned between ethyl acetate and water, with the pH adjusted to 12 by addition of 6N NaOH. The organic phase was washed with brine, dried over magnesium sulfate, and evaporated in vacuo to a crystalline solid, 1.29 g, 64% yield. NMR was consistent with structure. MS: APCI: M+1: 189.1 (M: 188.23).

4e. Synthesis of 4-(3-Chloro-phenyl)-1-methyl-6-[(3-methyl-3H-imidazol-4-yl)-phenyl-methoxy]-1H-quinolin-2-one

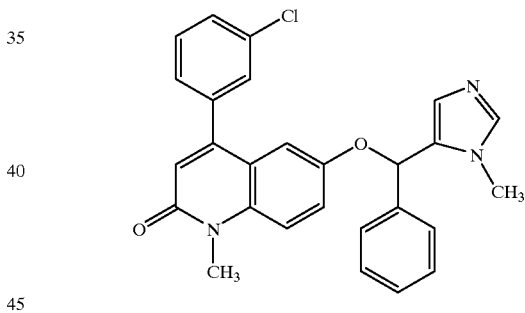

In a manner similar to that of (1), 4-(3-chloro-phenyl)-1-methyl-6-[(3-methyl-3H-imidazol-4-yl)-phenyl-methoxy]-1H-quinolin-2-one was prepared from (3-methyl-1H-imidazol-4-yl)-phenyl-methanol (0.66 g, 3.5 mmol), and 4-(3-chloro-phenyl)-6-hydroxy-1-methyl-1H-quinolin-2-one (0.857 g, 3.0 mmol). The resulting syrup was purified by silica gel chromatography, eluted with a gradient of 0 to 3% methanol in chloroform. The product was recovered as a foam, 0.577 g, 42% yield. The material was additionally purified by reverse phase chromatography eluted with acetonitrile and water with 0.5% trifluoroacetic acid buffer. Recovered 0.314 g, 23% yield. NMR was consistent with structure. MS: APCI: M+1: 456.1 (M: 455.9).

Analysis calculated for $C_{27}H_{22}N_3O_2Cl$, 0.75 $H_2O$, 1.3 $C_2HO_2F_3$: C, 57.55; H, 3.79; N, 6.80; $H_2O$, 2.19; F 11.99; Cl, 5.74. Found: C, 57.59; H, 3.84; N, 6.59; $H_2O$, 2.11; F 11.83; Cl, 6.02.

Example 5

Synthesis of 7-(2-Imidazol-1-yl-1-phenyl-ethoxy)-4-phenyl-chromen-2-one

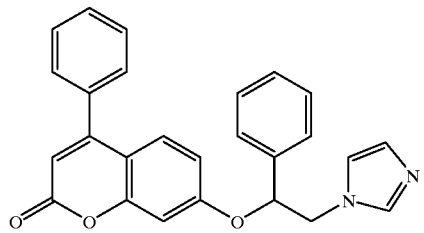

In a manner similar to that of (1 h), 7-(2-imidazol-1-yl-1-phenyl-ethoxy)-4-phenyl-chromen-2-one was prepared from (7-hydroxy-4-phenylcoumarin (Sigmna-Aldrich Corp., 2.0 g, 8.4 mmol), and 1 g 2-imidazol-1-yl-phenyl-ethanol (1.65 g, 8.8 mmol). The resulting foam was purified by silica gel chromatography, eluted with a gradient of 0% to 1% methanol in chloroform. The product was recovered as a foam, 0.84 g, 25% yield. NMR was consistent with structure. MS: APCI: M+1: 409.1 (M: 408.3).

Analysis calculated for $C_{26}H_{20}N_2O_3$, $0.5\ H_2O$ : C, 74.80; H, 5.07; N, 6.71; $H_2O$, 2.15. Found: C, 74.65; H, 5.29; N, 6.95; $H_2O$, 1.35.

Example 6

Synthesis of 4-(3-Chloro-phenyl)-7-(2-imidazol-1-yl-1-phenyl-ethoxy)-chromen-2-one

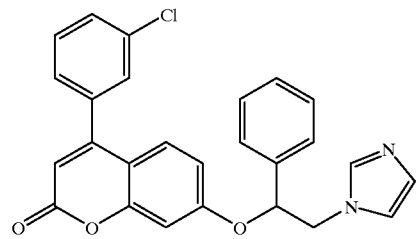

6a. Synthesis of 3-(3-Chloro-phenyl)-3-oxo-propionic acid ethyl ester

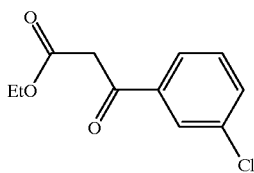

This synthesis was carried out as described in *Chem. Pharm. Bull.*, 1987;35(9):3909–3913. Sodium hydride (60% dispersion in mineral oil; 0.05 mol) was suspended in diethyl ether (50 mL), and diethyl carbonate (118.1 g/mol; 0.010 mol) was added. A solution of 3-chloroacetophenone (154.6 g/mol; 0.02 mol) in diethyl ether (20 mL) was then added dropwise. The reaction mixture was refluxed for 7 hours and stirred at room temperature overnight. The reaction mixture was poured into water (40 mL), acidified to pH 2 with 2N HCl, and extracted with ethyl acetate (3 times: 50 mL). The ethyl acetate solution was dried over $MgSO_4$, filtered, and concentrated to give 3.31 g (73% yield) of crude product. Purification was carried out by flash chromatography (silica gel: 145 g; eluent:chloroform) to give 0.51 g (11% yield) of the desired product. MS: APCI: M+1: 227.1 (M: 226).

6b. Synthesis of 4-(3-Chloro-phenyl)-7-hydroxy-chromen-2-one

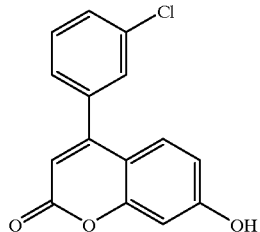

This synthesis was carried out as described in *Chem. Pharm. Bull.*, 1987;35(9):3909–3913. The product from Step 6a 3-(3-chloro-phenyl)-3-oxo-propionic acid ethyl ester (226 g/mol; 0.0023 mol) was dissolved in ethanol (20 mL). Resorcinol (110.1 g/mol; 0.0023 mol) was added, and the solution was cooled to 0° C. The solution was saturated with HCl gas, and stirred for 1 hour at 0° C., and for 3 days at room temperature, under a nitrogen atmosphere. The reaction mixture was poured in water (25 mL) and the solution extracted with ethyl acetate (3 times: 50 mL). The ethyl acetate solution was dried over $MgSO_4$, filtered, and concentrated to give 0.69 g (quantitative yield) of crude product. Purification was carried out by flash chromatography (silica gel: 45 g; eluent: 1:1/ethyl acetate:hexanes) to give 0.42 g (67% yield) of the desired product. MS: APCI: M+1: 273.0 (M: 272).

6c. Synthesis of 4-(3-Chloro-phenyl)-7-(2-imidazol-1-yl-1-phenyl-ethoxy)-chromen-2-one

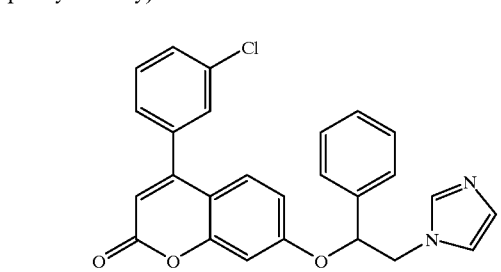

The product from 6b, 4-(3-chloro-phenyl)-7-hydroxy-chromen-2-one (272 g/mol; 0.001 mol) was dissolved in dry THF (25 mL) and triphenylphosphine (262.3 g/mol; 0.0015 mol) was added followed by 2-imidazol-1-yl-1-phenyl-ethanol (188.7 g/mol; 0.0012 mol). A solution of DEAD (174.2 g/mol; 0.0019 mol) in dry THF (5 mL) was added dropwise at room temperature, under a nitrogen atmosphere. The reaction was stirred overnight at room temperature under a nitrogen atmosphere. Ethyl acetate (50 mL) was added to the reaction mixture, and the organic layer was washed with water (3 times: 50 mL), brine (2 times: 50 mL), dried over $MgSO_4$, filtered, and concentrated to give 1.4 g (quantitative yield ) of crude product. Purification was carried out by flash chromatography (silica gel: 58 g; eluent: 95:5/chloroform:methanol) to give 0.31 g (70% yield) of the desired product. Purification by preparative HPLC was then carried out (reversed phase HPLC, C 18-column (22×250 mm, 0.1 mm, 300 Å), gradient: 10% to 50% acetonitrile (0.1% TFA) against 0.1% aqueous TFA; 100 minutes; 13 mL/minute) to give 15 mg (4% yield) of the desired product. MS: APCI: M+1: 443.1 (M: 442).

Analysis calculated for $C_{26}H_{19}N_2O_3Cl$, 1.45 $CF_3COOH$, 1.19 $H_2O$: C, 55.13; H, 3.65; N, 4.45. Found: C, 55.15; H, 3.66; N, 4.22.

Example 7

Synthesis of 7-(2-Imidazol-1-yl-1-phenyl-ethoxy)-4-m-tolyl-chromen-2-one

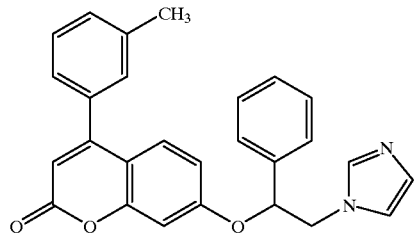

The title compound was prepared according to (6), in Step 6a, substituting 3-methylacetophenone for 3-chloroacetophenone, to give 0.137 g (25% yield). MS: APCI: M+1: 423.3 (M: 422).

Analysis calculated for $C_{27}H_{22}N_2O_3$, 1.36 $CF_3COOH$, 0.60 $H_2O$: C, 60.67; H, 4.21; N, 4.76. Found: C, 60.66; H, 3.85; N, 4.68.

Example 8

Synthesis of 7-(2-Imidazol-1-yl-1-phenyl-ethoxy)-4-o-tolyl-chromen-2-one

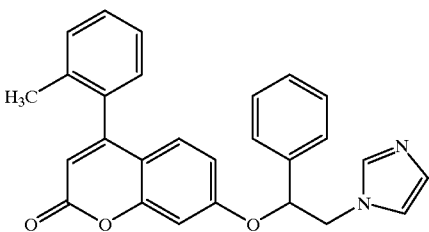

The title compound was prepared according to (6) above, in Step 6a, substituting 2-methylacetophenone for 3-chloroacetophenone, to give 0.015 g (1% yield). MS: APCI: M+1: 423.2 (M: 422).

Analysis calculated for $C_{27}H_{22}N_2O_3$, 1.21 $CF_3COOH$, 1.50 $H_2O$: C, 60.15; H, 4.50; N, 4.77. Found: C, 59.80; H, 4.10; N, 5.30.

Example 9

Synthesis of 4-(4-Chloro-phenyl)-7-(2-imidazol-1-yl-1-phenyl-ethoxy)-chromen-2-one

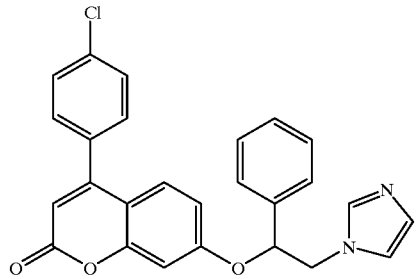

The title compound was prepared according to (6), in Step 6a, substituting 4-chloroacetophenone for 3-chloroacetophenone, to give 0.010 g (2.4% yield). MS: APCI: M+1: 443.2 (M: 442).

Analysis calculated for $C_{26}H_{19}N_2O_3Cl$, 0.99 $CF_3COOH$, 0.29 $H_2O$, 4.50 $CH_3OH$: C, 55.32; H, 5.51; N, 3.97. Found: C, 55.70; H, 5.20; N, 3.50.

Example 10

Synthesis of 4-(2-Chloro-phenyl)-7-(2-imidazol-1-yl-1-phenyl-ethoxy)-chromen-2-one

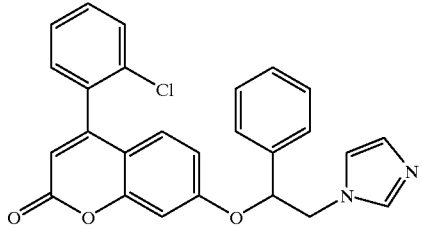

The title compound was prepared according to (6) above, in Step 6a, substituting 2-chloroacetophenone for 3-chloroacetophenone, to give 0.007 g (1% yield). MS: APCI: M+1: 443.2 (M: 442).

Analysis calculated for $C_{26}H_{19}N_2O_3Cl$, 1.22 $CF_3COOH$, 2.24 $H_2O$: C, 54.89; H, 4.00; N, 4.50. Found: C, 54.50; H, 3.60; N, 4.90.

Example 11

Synthesis of 7-(2-imidazol-1-yl-1-phenyl-ethoxy)-4-p-totyl-chromen-2-one

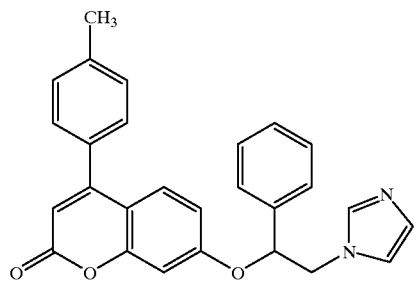

The title compound was prepared according to (6) above, in Step 6a, substituting 3-methylacetophenone for 3-chloroacetophenone, to give 0.044 g (5% yield). MS: APCI: M+1: 423.1 (M: 422).

Analysis calculated for $C_{27}H_{22}N_2O_3$, 1.39 $CF_3COOH$: C, 61.57; H, 4.06; N, 4.82. Found: C, 61.40; H, 4.40; N, 4.90.

Example 12

Synthesis of 8-allyl-7-(2-imidazol-1-yl-1-phenyl-ethoxy)-4-phenyl-chromen-2-one

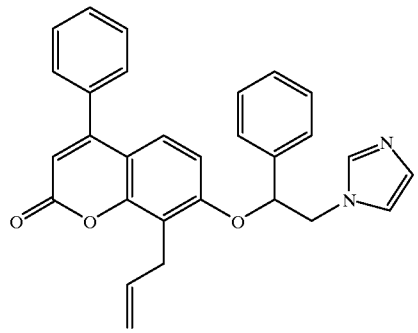

12a. Synthesis of 7-hydroxy-4-phenyl-chromen-2-one

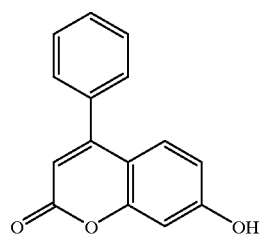

The title compound was prepared according to (6a, 6b) above, in Step 6a, substituting acetophenone for 3-chloroacetophenone, to give the corresponding phenol derivative (3 g, 65% yield), MS: APCI: M+1: 239.1 (M: 238).

12b. Synthesis of 7-allyloxy-4-phenyl-chromen-2-one

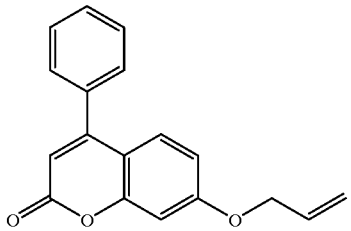

The product from 12a (3 g, 0.0126 mol) was dissolved in dimethylformamide (25 mL), and cesium carbonate (3.1 g, 0.00945 mol) was added followed by allyl bromide (1.2 mL, 0.0139 mol). The reaction was stirred at 80° C. for 5 hours. The precipitated solid was filtered, and the filtrate was concentrated under reduced pressure. The residue was taken up in diethyl ether, and the organic solution was washed twice with 1N citric acid, saturated sodium bicarbonate, and brine. It was dried over $MgSO_4$, filtered, and concentrated to give 2 g (57% yield) of crude product. Purification was carried out by flash chromatography (silica gel: 90 g; eluent: 1:1/hexanes:ethyl acetate) to give 1.33 g (38% yield) of the desired product. MS: APCI: M+1: 279.1 (M: 278).

12c. Synthesis of 8-allyl-7-hydroxy-4-phenyl-chromen-2-one

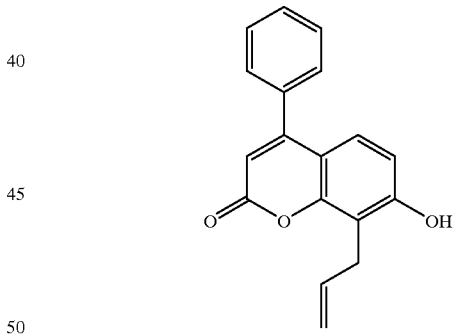

The product from 12b was dissolved in N,N-diethyl aniline (15 mL) and the solution heated to 210° C. overnight. The reaction mixture was concentrated under reduced pressure and ethyl acetate (20 mL) was added to the residue. The precipitated solid was filtered, washed with diethyl ether. The filtrate was diluted with ethyl acetate, and the organic solution was washed three times with 2N HCl, and brine. It was dried over $MgSO_4$, filtered, and concentrated to give 0.34 g (25% yield) of the desired product. MS: APCI: M+1: 279.1 (M: 278).

12d. Synthesis of 8-allyl-7-(2-imidazol-1-yl-1-phenyl-ethoxy)-4-phenyl-chromen-2-one

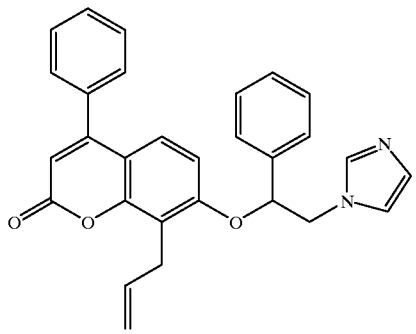

The synthesis of the title compound was prepared according to (6c) above, to give 0.20 g (36% yield). MS: APCI: M+1: 449.1 (M: 448.5).

Analysis calculated for $C_{29}H_{24}N_2O_3$, 0.1 $H_2O$, 0.23 $CH_2Cl_2$: C, 74.72; H, 5.29; N, 5.96. Found: C, 74.71; H, 5.20; N, 6.20.

BIOLOGICAL ASSAYS

PFT Inhibitory Activity

The protein farnesyl transferase (PFT) or farnesyl protein transferase (FPT) inhibitory activity of compounds of the present invention were assayed in HEPES buffer (pH 7.4) containing 5 mM potassium phosphate and 20 μM $ZnCl_2$. The solution also contained 5 mM DTT (dithiothreitol), 5 mM $MgCl_2$, and 0.1% PEG 8000. Assays were performed in 96-well plates (Wallec, Finland) and employed solutions composed of varying concentrations of a compound of the present invention in 10% DMSO (dimethylsulfoxide). Upon addition of both substrates, radiolabeled farnesyl pyrophosphate ([$1^3H$], specific activity 15–30 Ci/mmol, final concentration 134 nM) and (biotinyl)-Ahe-Thr-Lys-Cys-Val-Ile-Met ([3aS[3a α, 4 β, 6a α]-hexahydro-2-oxo-1H-thieno[3,4-d]imidazole-5-pentanoicacid]-[7-aminoheptanoic acid]-Thr-Lys-Cys-Val-Ile-Met). Ahe is 7-aminoheptanoic acid, Thr is threonine, Lys is lysine, Cys is cysteine, Val is valine, Ile is isoleucine, and Met is methionine (final concentration 0.2 μM); the enzyme reaction was started by addition of SF9 affinity purified rat FPT. After incubation at 30° C. for 30 minutes, the reaction was terminated by diluting the reaction 2.5-fold with a stop buffer containing 1.5 M magnesium acetate, 0.2 M $H_3PO_4$, 0.5% BSA (bovine serum albumin), and strepavidin beads (Amersham, Arlington Heights, Ill.) at a concentration of 1.3 mg/mL. After allowing the plate to settle for 30 minutes at room temperature, radioactivity was quantitated on a microBeta counter (Model 1450, Wallec, Finland). The assay was also carried out without 5 mM potassium phosphate.

Mobility Shift Assay

Twenty-four hours after planting 2×10⁶ ras-transformed cells per treatment condition, the farnesylation inhibitor is added at varying concentrations. Following an 18-hour incubation period, cells are lysed in phosphate-buffered saline containing 1% Triton X-100, 0.5% sodium deoxycholate, and 0.1% SDS (sodium dodecyl sulfate), pH 7.4 in the presence of several protease inhibitors (PMSF (phenylmethylsulfonylfluoride), antipain, leupeptin, pepstatin A, and aprotinin all at 1 μg/mL). Ras protein is immunoprecipitated from the supernatants by the addition of 3 μg v-H-ras Ab-2 (Y13-259 antibody from Oncogene Science, Cambridge, Mass.). After overnight immunoprecipitation, 30 μL of a 50% protein G-Sepharose slurry (Pharmacia, Uppsala, Sweden) is added followed by 45-minute incubation. Pellets are resuspended in 2X tris-glycine loading buffer (Novex, San Diego, Calif.) containing 5% mercaptoethanol and then denatured by 5 minutes boiling prior to electrophoresis on 14% Tris-glycine SDS gels. Using Western transfer techniques, proteins are transferred to nitrocellulose membranes followed by blocking in blocking buffer. Upon overnight incubation with primary antibody (pan-ras Ab-2 from Oncogene Science, Cambridge, Mass.), an antimouse HRP (horseradish peroxidase) conjugate secondary antibody (Amersham) is employed for detection of the ras protein. Blots are developed using ECL (enhanced chemiluminescence) techniques (Amersham, Arlington Heights, Ill.).

The results of these assays are presented in the following table.

| Example Number | IC$_{50}$ (μM) Hepes + 5 mM Phosphate | IC$_{50}$ (μM) Hepes | Mobility Shift MED (μM) |
|---|---|---|---|
| 1 | 0.068 | 0.064 | 1 |
| 2 | 0.99 | 0.7 | >1 |
| 3 | 3.6 | 9.8 | NT |
| 4 | 1.8 | 1.7 | NT |
| 5 | 0.8 | 0.74 | 0.2 |
| 6 | 0.32 | 0.29 | 1 |
| 7 | 1.4 | 0.5 | NT |
| 8 | 0.92 | 0.98 | NT |
| 9 | 1.6 | 1.8 | NT |
| 10 | 0.29 | 0.14 | >0.2 |
| 11 | 0.52 | 0.67 | 1 |
| 12 | 0.64 | 0.63 | >1 |

NT = Not Tested.

What is claimed is:

1. A compound having the Formula I:

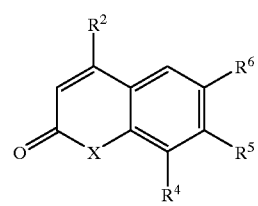

and the pharmaceutically acceptable salts thereof, wherein

X is —N—$R^3$ or O;

$R^2$ is alkyl, alkenyl, aryl, substituted aryl, aralkyl, substituted aralkyl, heteroaryl, substituted heteroaryl, heteroaralkyl, or substituted heteroaralkyl;

$R^3$ is hydrogen, alkyl, alkenyl, aralkyl, substituted aralkyl, aryl, or substituted aryl;

$R^4$ is hydrogen, alkyl, alkenyl, aryl, substituted aryl, aralkyl, substituted aralkyl, heteroaralkyl, or substituted heteroaralkyl;

one of $R^5$ and $R^6$ is hydrogen, and the other is —O—$R^1$;

$R^1$ is

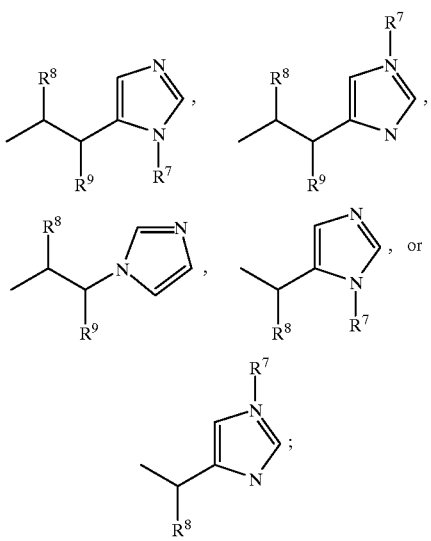

$R^7$ is hydrogen, alkyl, aralkyl or substituted aralkyl; and
$R^8$ and $R^9$ are independently hydrogen, alkyl, aryl, substituted aryl, heteroaryl, substituted heteroaryl, aralkyl, or substituted aralkyl;

provided, however, that when $R^2$ is hydrogen or $C_1-C_6$ alkyl, X is O, $R^4$ is hydrogen, $R^5$ or $R^6$ is —O—$R^1$, and $R^1$ is

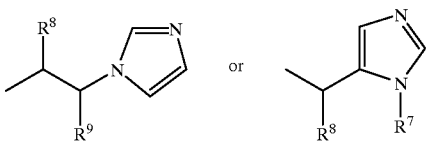

then, $R^7$, $R^8$, and $R^9$ are not all hydrogen.

2. A compound in accordance with claim 1 wherein X is O or —N—$CH_3$.

3. A compound in accordance with claim 1 wherein $R^2$ is chlorophenyl, phenyl, or methylphenyl.

4. A compound in accordance with claim 1 wherein $R^4$ is hydrogen, alkyl, alkenyl, aralkyl, or heteroaralkyl.

5. A compound in accordance with claim 1 wherein $R^8$ is phenyl, and $R^9$ is hydrogen.

6. A compound in accordance with claim 1 wherein $R^7$ is hydrogen, benzyl, or methyl.

7. A compound in accordance with claim 1 wherein
$R^2$ is chlorophenyl, phenyl, or methylphenyl; and
$R^4$ is hydrogen, alkyl, alkenyl, aralkyl, or heteroaralkyl.

8. A compound selected from the group consisting of:

4-(3-Chloro-phenyl)-6-(2-imidazol-1-yl-1-phenyl-ethoxy)-1-methyl-8-propyl-1H-quinolin-2-one;

4-(3-Chloro-phenyl)-6-(2-imidazol-1-yl-1-phenyl-ethoxy)-1-methyl-8-phenethyl-1H-quinolin-2-one;

6-[2-(3-Benzyl-3H-imidazol-4-yl)-ethoxy]-4-(3-chloro-phenyl)-1-methyl-1H-quinolin-2-one;

6-[2-(3-Benzyl-3H-imidazol-4-yl)-ethoxy]-4-(3-chloro-phenyl)-1-methyl-8-propyl-1H-quinolin-2-one;

6-[2-(3-Benzyl-3H-imidazol-4-yl)-ethoxy]-4-(3-chloro-phenyl)-1-methyl-8-phenethyl-1H-quinolin-2-one;

4-(3-Chloro-phenyl)-7-(2-imidazol-1-yl-1-phenyl-ethoxy)-1-methyl-8-propyl-1H-quinolin-2-one;

4-(3-Chloro-phenyl)-7-(2-imidazol-1-yl-1-phenyl-ethoxy)-1-methyl-8-phenethyl-1H-quinolin-2-one;

7-[2-(3-Benzyl-3H-imidazol-4-yl)-ethoxy]-4-(3-chloro-phenyl)-1-methyl-1H-quinolin-2-one;

7-[2-(3-Benzyl-3H-imidazol-4-yl)-ethoxy]-4-(3-chloro-phenyl)-1-methyl-8-propyl-1H-quinolin-2-one;

7-[2-(3-Benzyl-3H-imidazol-4-yl)-ethoxy]-4-(3-chloro-phenyl)-1-methyl-8-phenethyl-1H-quinolin-2-one;

4-(2-Chloro-phenyl)-7-(2-imidazol-1-yl-1-phenyl-ethoxy)-8-propyl-chromen-2-one;

4-(2-Chloro-phenyl)-7-(2-imidazol-1-yl-1-phenyl-ethoxy)-8-phenethyl-chromen-2-one;

7-[2-(3-Benzyl-3H-imidazol-4-yl)-ethoxy]-4-(2-chloro-phenyl)-chromen-2-one;

7-[2-(3-Benzyl-3H-imidazol-4-yl)-ethoxy]-4-(2-chloro-phenyl)-8-propyl-chromen-2-one; and 7-[2-(3-Benzyl-3H-imidazol-4-yl)-ethoxy]-4-(2-chloro-phenyl)-8-phenethyl-chromen-2-one.

9. A pharmaceutically acceptable composition comprising a compound of claim 1.

10. A pharmaceutically acceptable composition comprising a compound of claim 8.

11. A method of treating or preventing restenosis or atherosclerosis, the method comprising administering to a patient having restenosis or atherosclerosis or at risk of having restenosis or atherosclerosis a therapeutically effective amount of a compound of claim 1.

12. A method of treating or preventing restenosis or atherosclerosis, the method comprising administering to a patient having restenosis or atherosclerosis or at risk of having restenosis or atherosclerosis a therapeutically effective amount of a compound of claim 8.

13. A method of treating cancer, the method comprising administering to a patient having cancer a therapeutically effective amount of a compound of claim 1.

14. A method of treating cancer, the method comprising administering to a patient having cancer a therapeutically effective amount of a compound of claim 8.

* * * * *